United States Patent
Kavuru

(10) Patent No.: US 10,730,836 B2
(45) Date of Patent: Aug. 4, 2020

(54) FORMS OF APREMILAST

(71) Applicant: Johnson Matthey Public Limited Company, London (GB)

(72) Inventor: Padmini Kavuru, Townsend, MA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 16/555,651

(22) Filed: Aug. 29, 2019

(65) Prior Publication Data

US 2020/0010416 A1    Jan. 9, 2020

Related U.S. Application Data

(62) Division of application No. 16/212,264, filed on Dec. 6, 2018, now abandoned, which is a division of application No. 15/186,687, filed on Jun. 20, 2016, now Pat. No. 10,196,355.

(51) Int. Cl.
    *C07D 209/48* (2006.01)

(52) U.S. Cl.
    CPC ........ *C07D 209/48* (2013.01); *C07B 2200/13* (2013.01)

(58) Field of Classification Search
    CPC .................................................. C07D 209/48
    See application file for complete search history.

(56) References Cited

U.S. PATENT DOCUMENTS

| | | |
|---|---|---|
| 5,215,758 A | 6/1993 | Krishnamurthy |
| 6,020,358 A | 2/2000 | Muller et al. |
| 7,427,638 B2 | 9/2008 | Muller et al. |
| 7,893,101 B2 | 2/2011 | Muller et al. |
| 9,351,957 B2 | 5/2016 | Khera et al. |
| 9,850,205 B2 | 12/2017 | Luo et al. |
| 2013/0217918 A1 | 8/2013 | Venkateswaralu et al. |
| 2014/0081032 A1 | 3/2014 | Connolly et al. |
| 2015/0283249 A1 | 10/2015 | Khera et al. |

FOREIGN PATENT DOCUMENTS

| | | |
|---|---|---|
| WO | 2009120167 A1 | 10/2009 |
| WO | 2012097116 A2 | 7/2012 |
| WO | 2014072259 A1 | 5/2014 |

OTHER PUBLICATIONS

Cancer [online], [retrieved on Jul. 6, 2007]. Retrieved from the Internet, URL http://www.nim.nih.gov/medlineplus/cancer.html>.
Golub et al; "Molecular Classification of Cancer: Class Discovery and Class Prediction by Gene Expression Monitoring", Science, 1999 vol. 286 pp. 531-537.
Lala et al; "Role of Nitric Oxide in Tumor Progression: Lessons from Experimental Tumors", Cancer and Metastasis Reviews (1998), 17(1) pp. 91-106.

*Primary Examiner* — Shawquia Jackson

(57) ABSTRACT

The present disclosure is directed to novel forms of apremilast and pharmaceutical compositions comprising any of the novel forms of apremilast. Also provided are processes for the preparation of novel forms of apremilast.

9 Claims, 19 Drawing Sheets

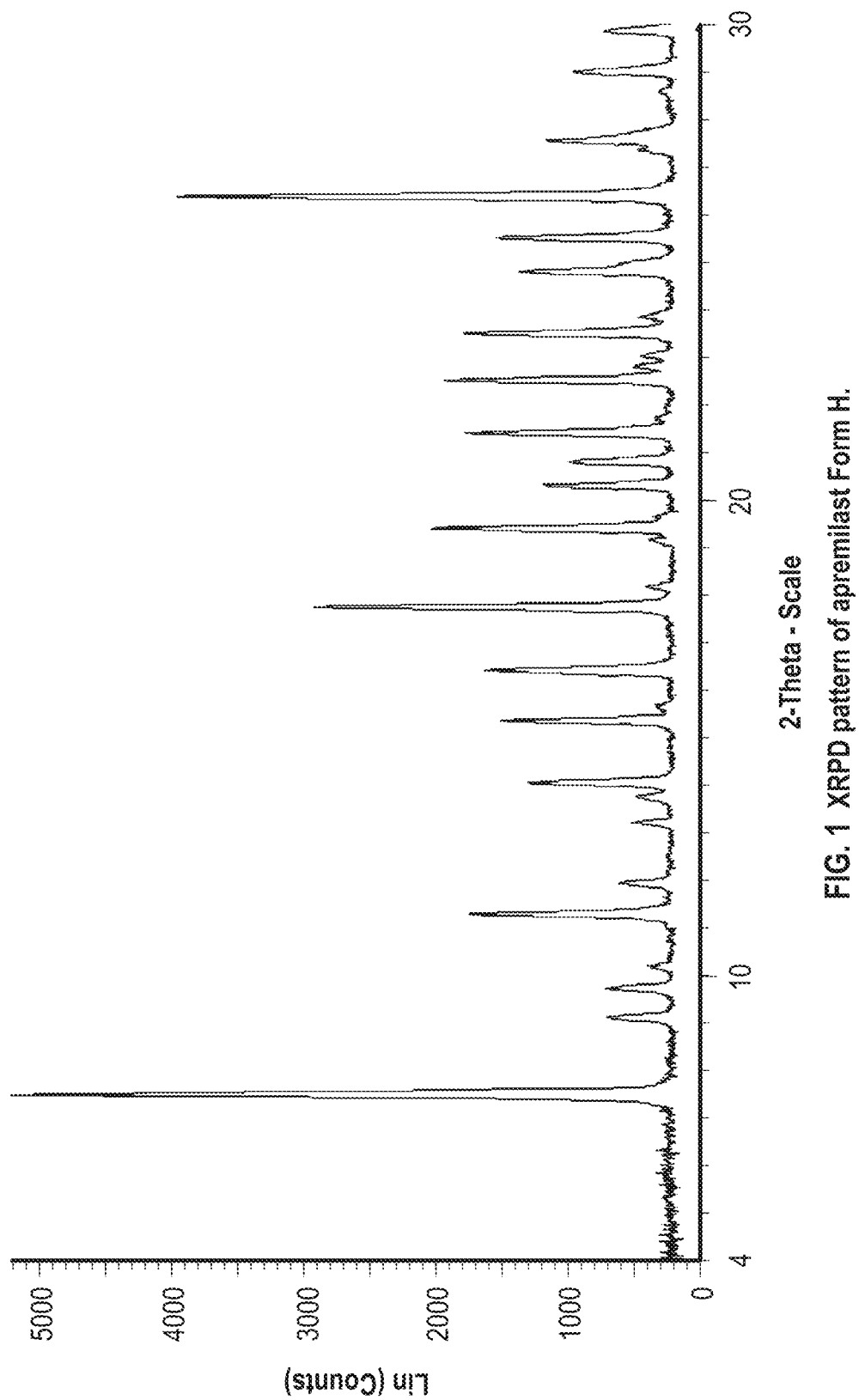
FIG. 1 XRPD pattern of apremilast Form H.

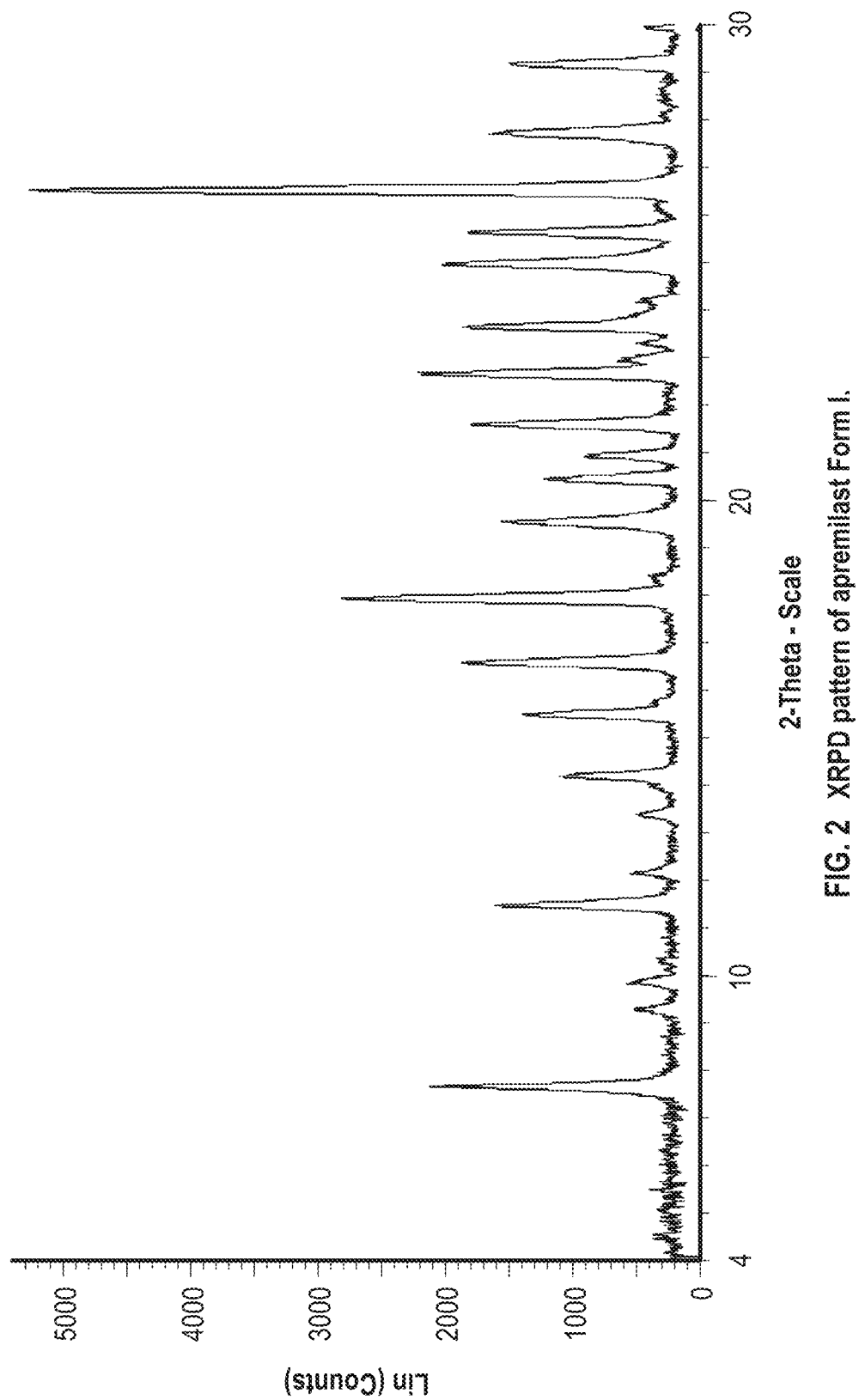
FIG. 2 XRPD pattern of apremilast Form I.

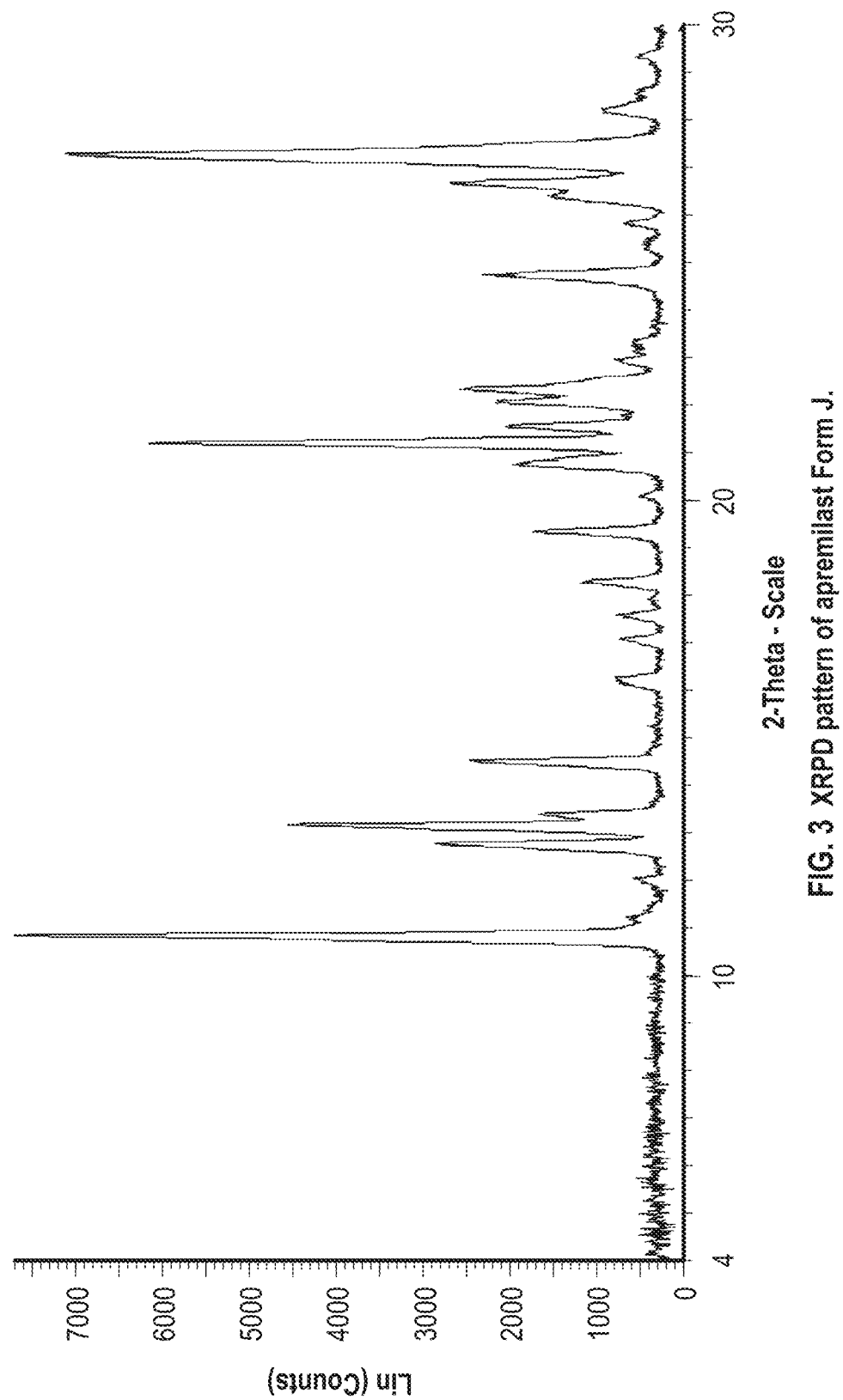
FIG. 3 XRPD pattern of apremilast Form J.

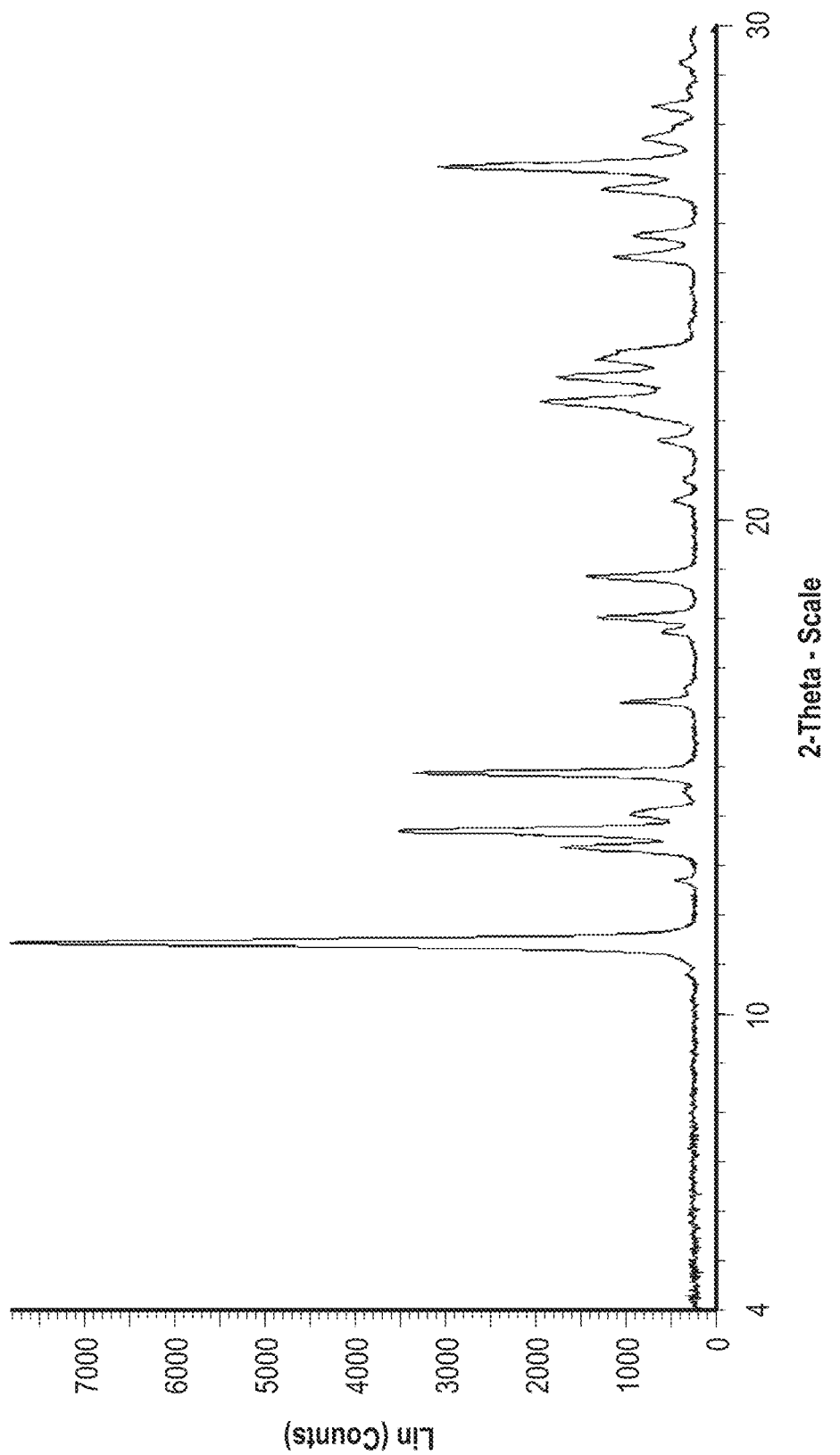
FIG. 4 XRPD pattern of apremilast Form K.

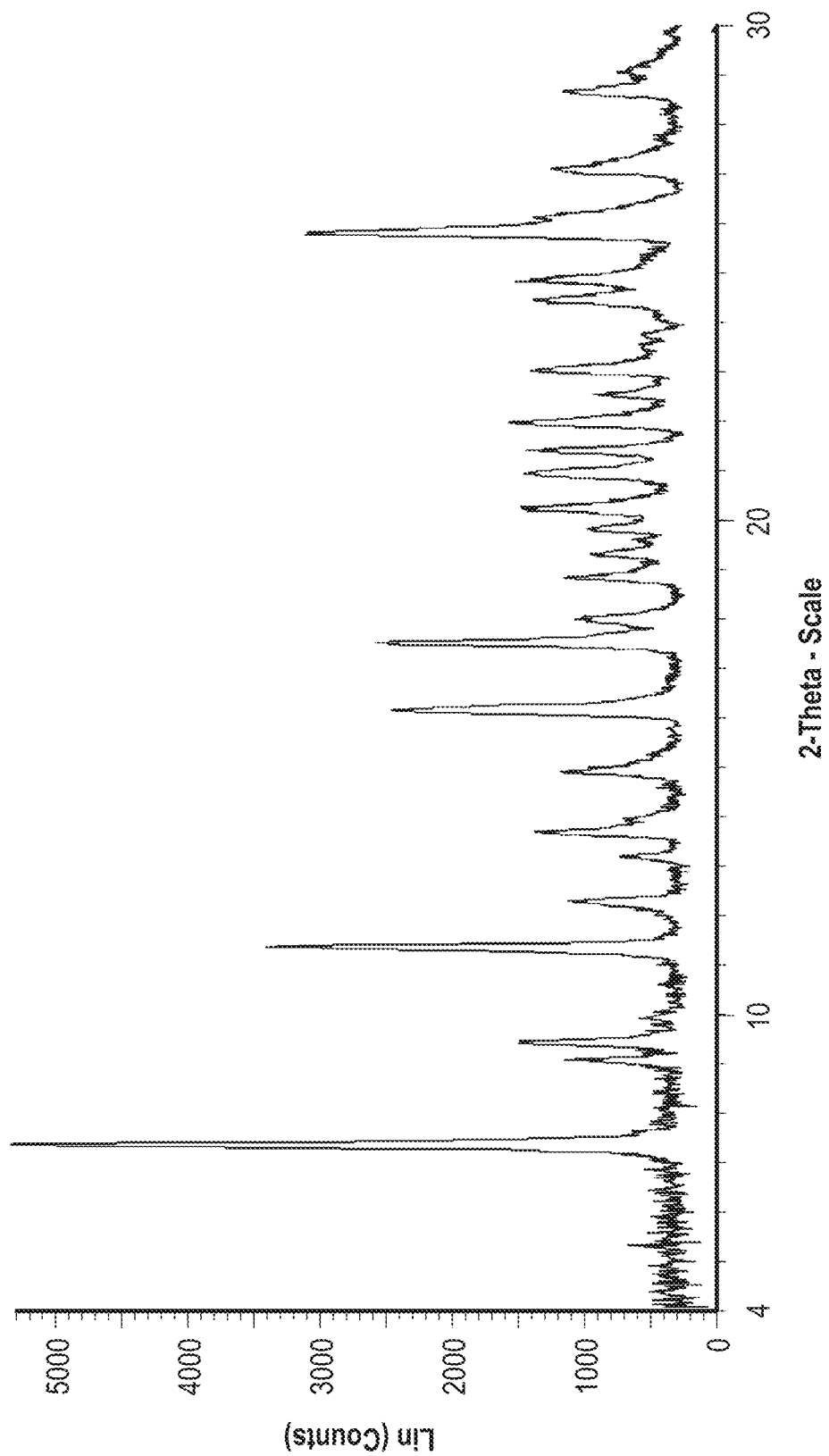

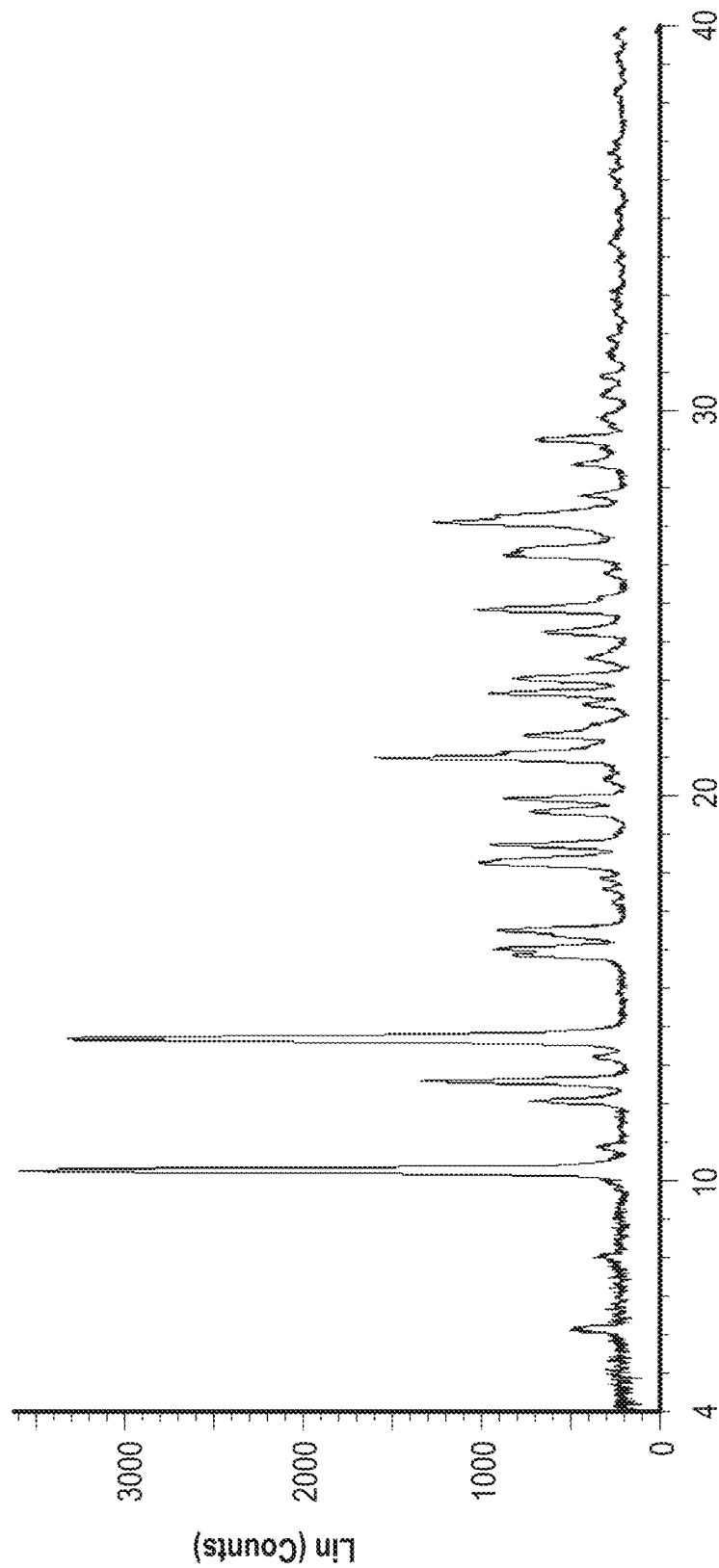
FIG. 6 XRPD pattern of apremilast.

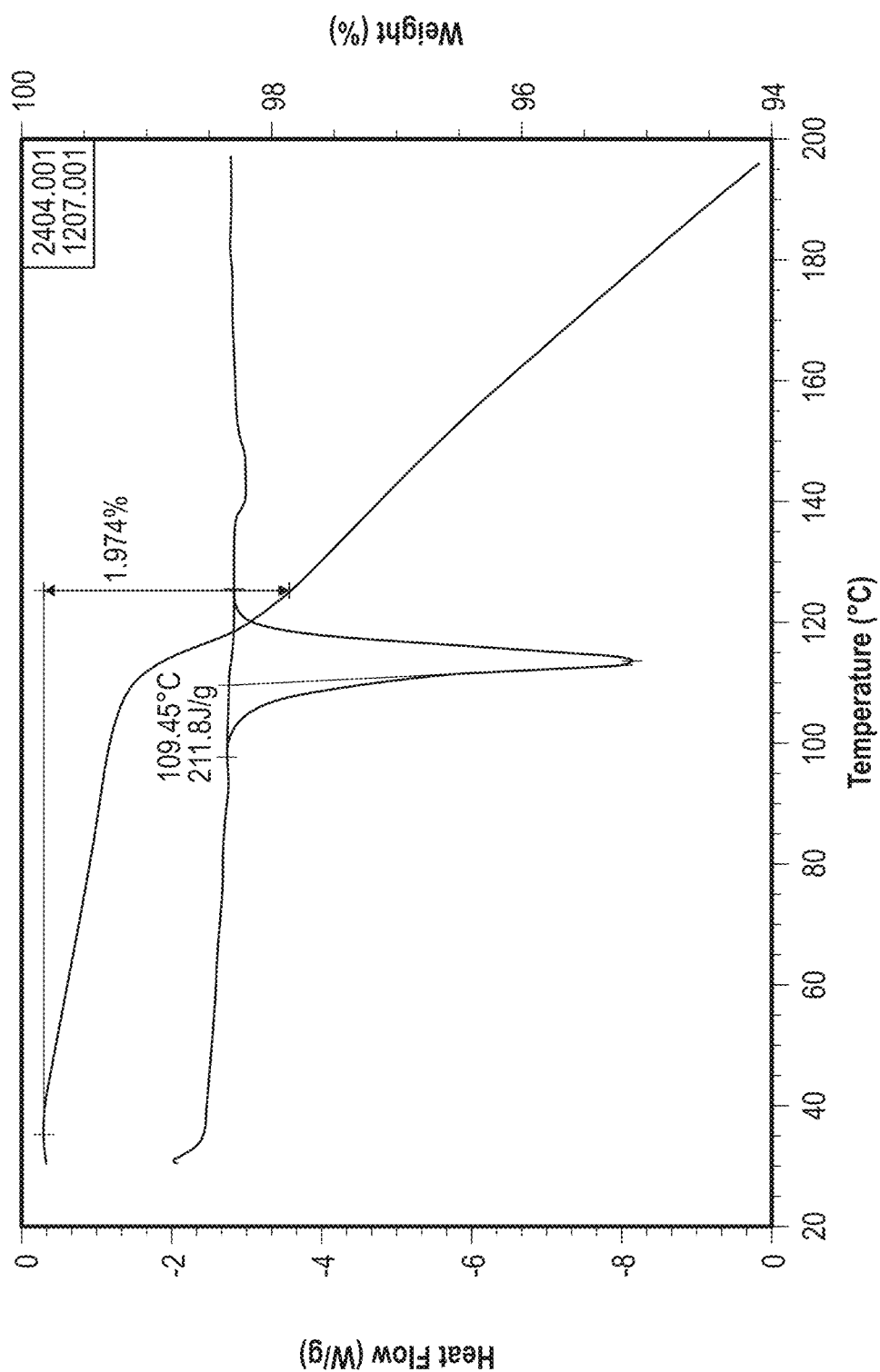
FIG. 7 DSC and TGA plot of apremilast Form H.

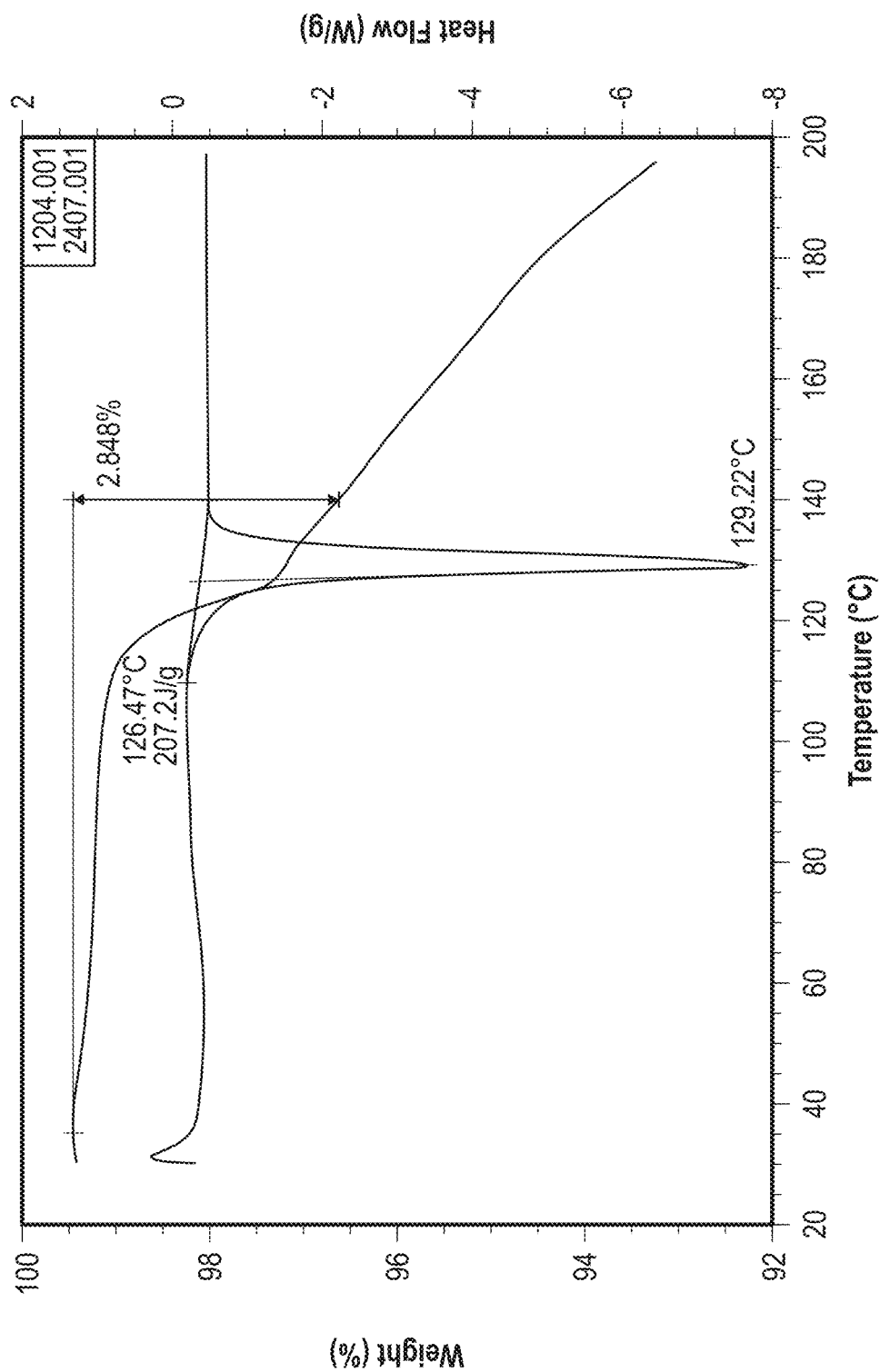
FIG. 8 DSC and TGA plot of apremilast Form I.

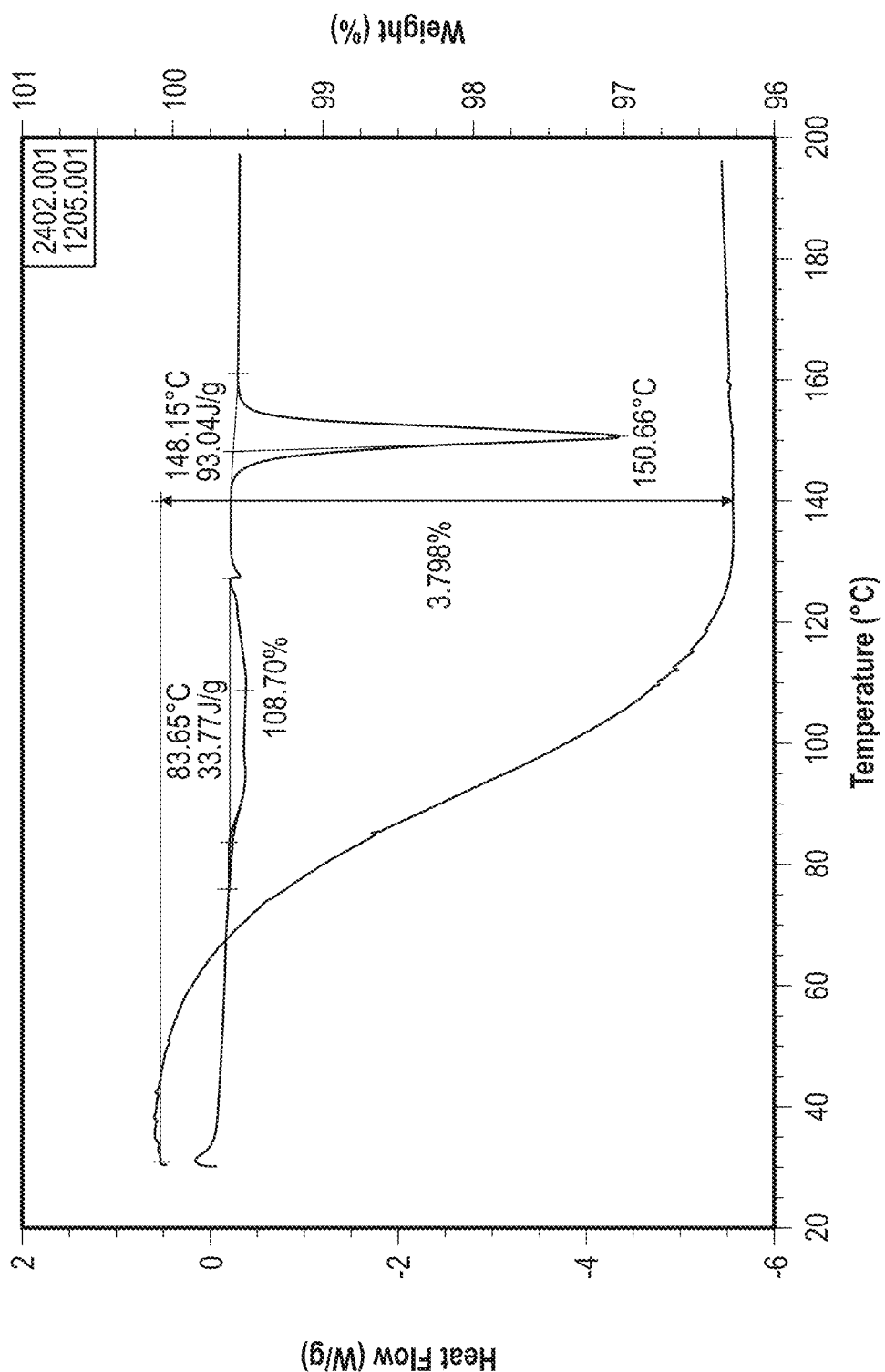
FIG. 9 DSC and TGA plot of apremilast Form J.

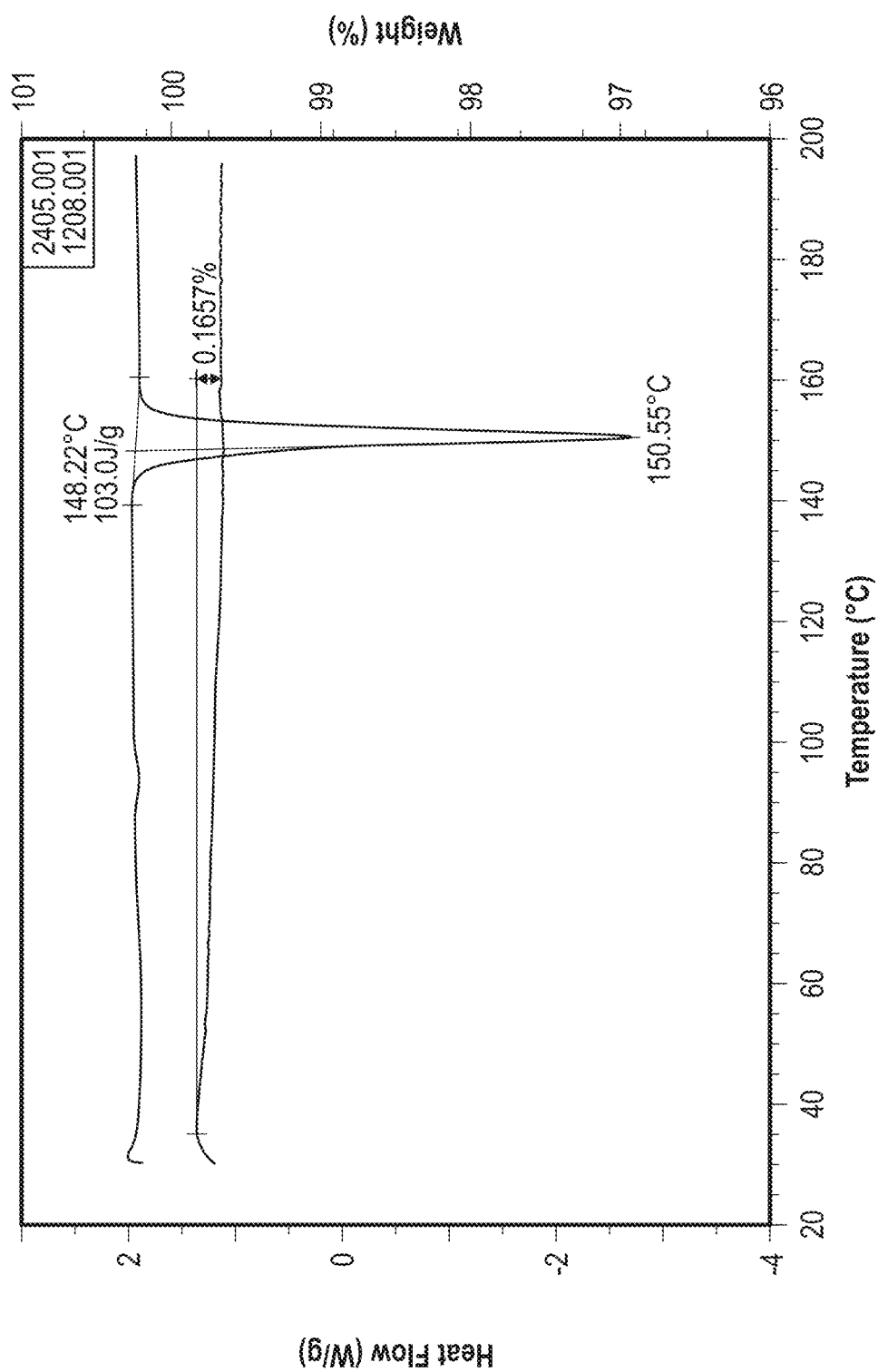
FIG. 10 DSC and TGA plot of apremilast Form K.

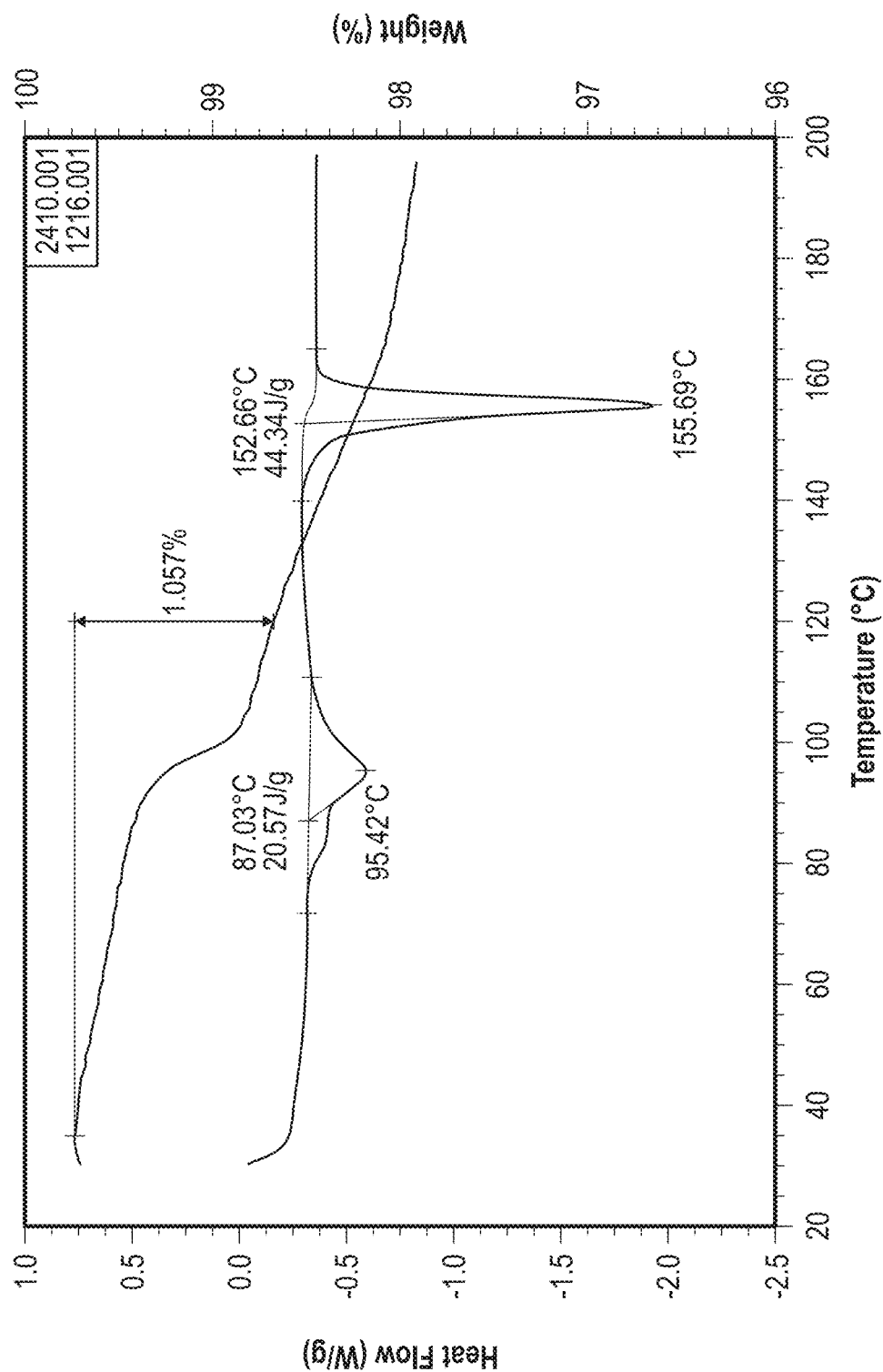
FIG. 11 DSC and TGA plot of apremilast Form M.

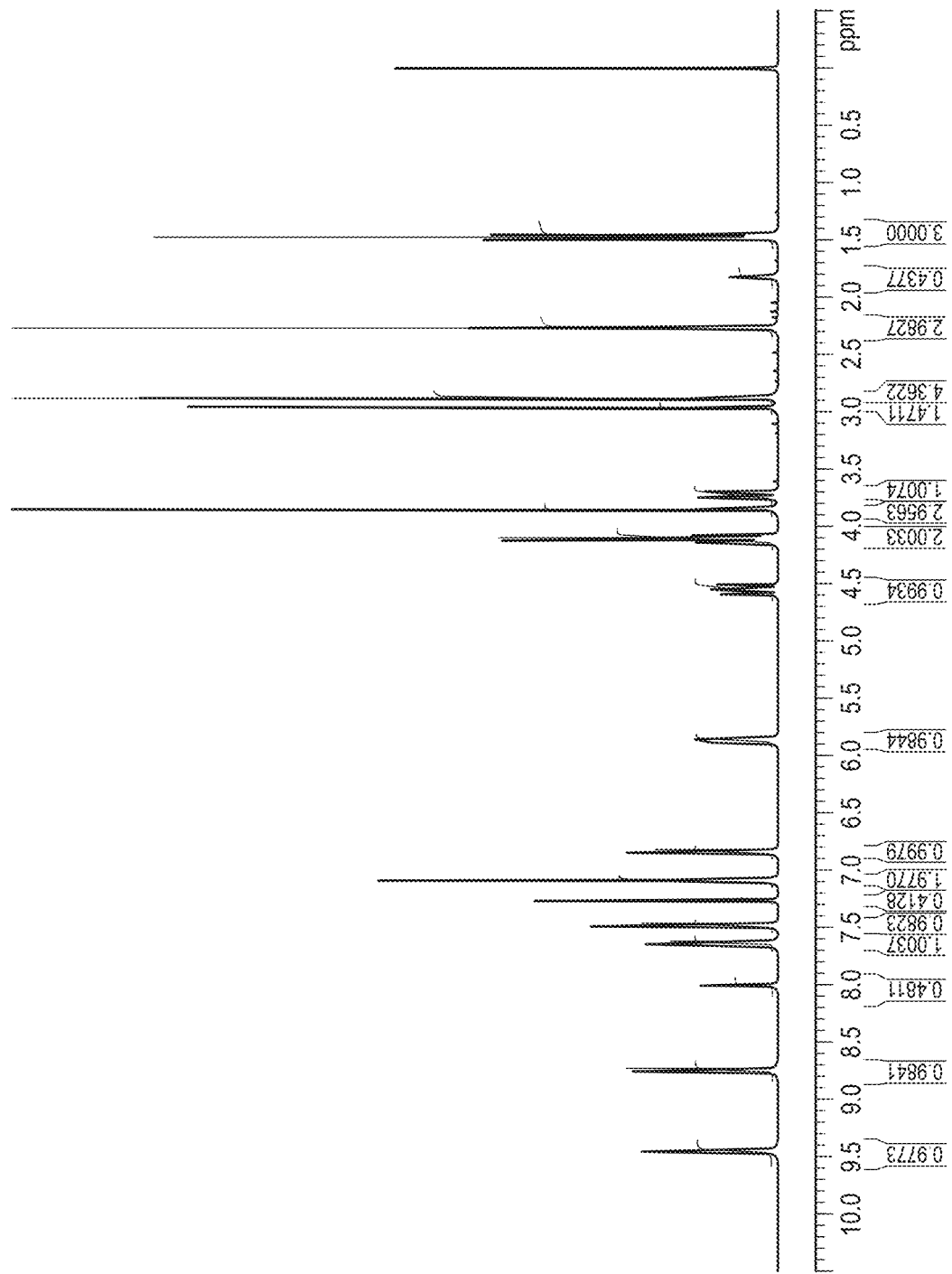
FIG. 12 1H-NMR plot of apremilast Form H.

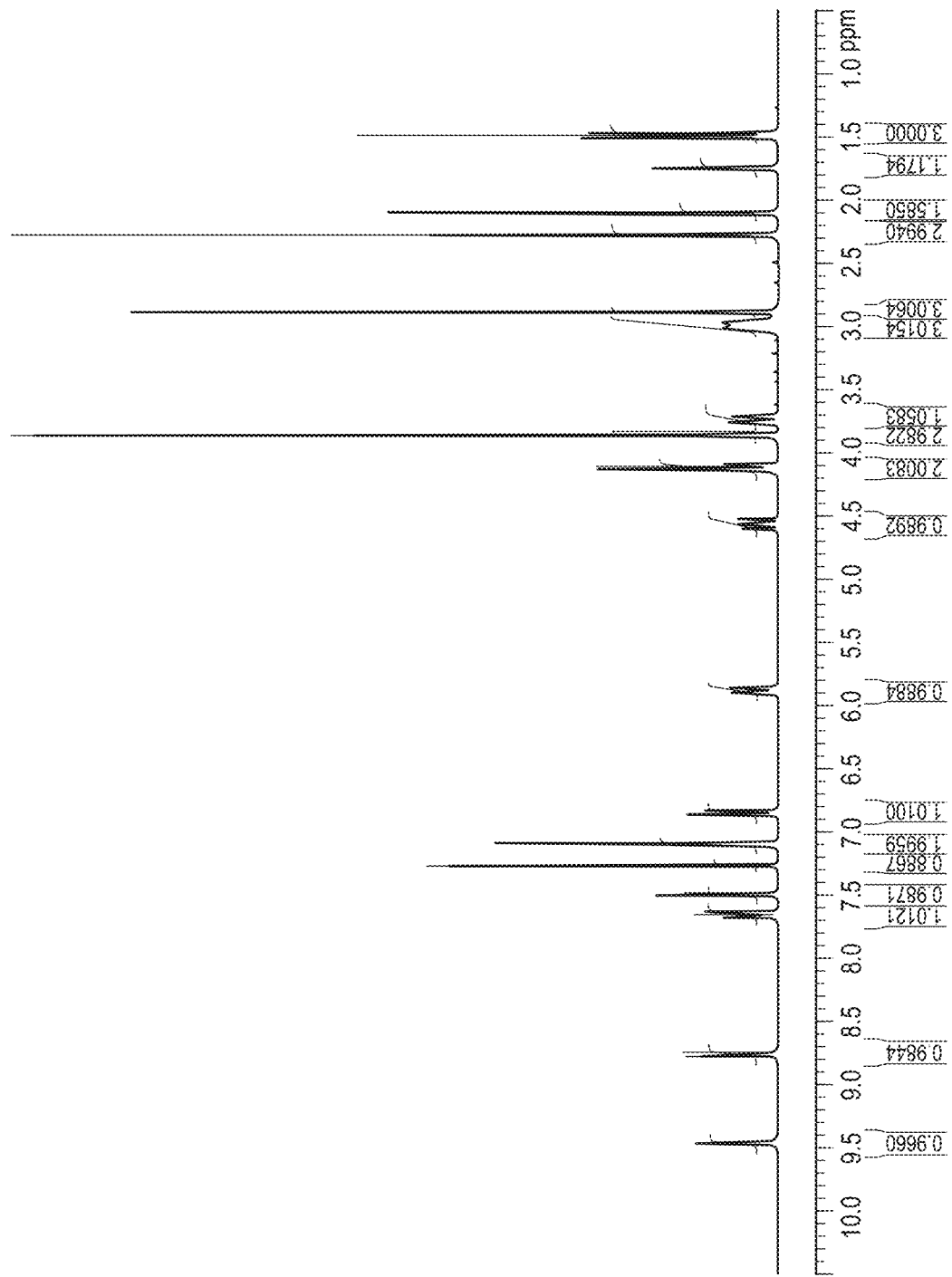

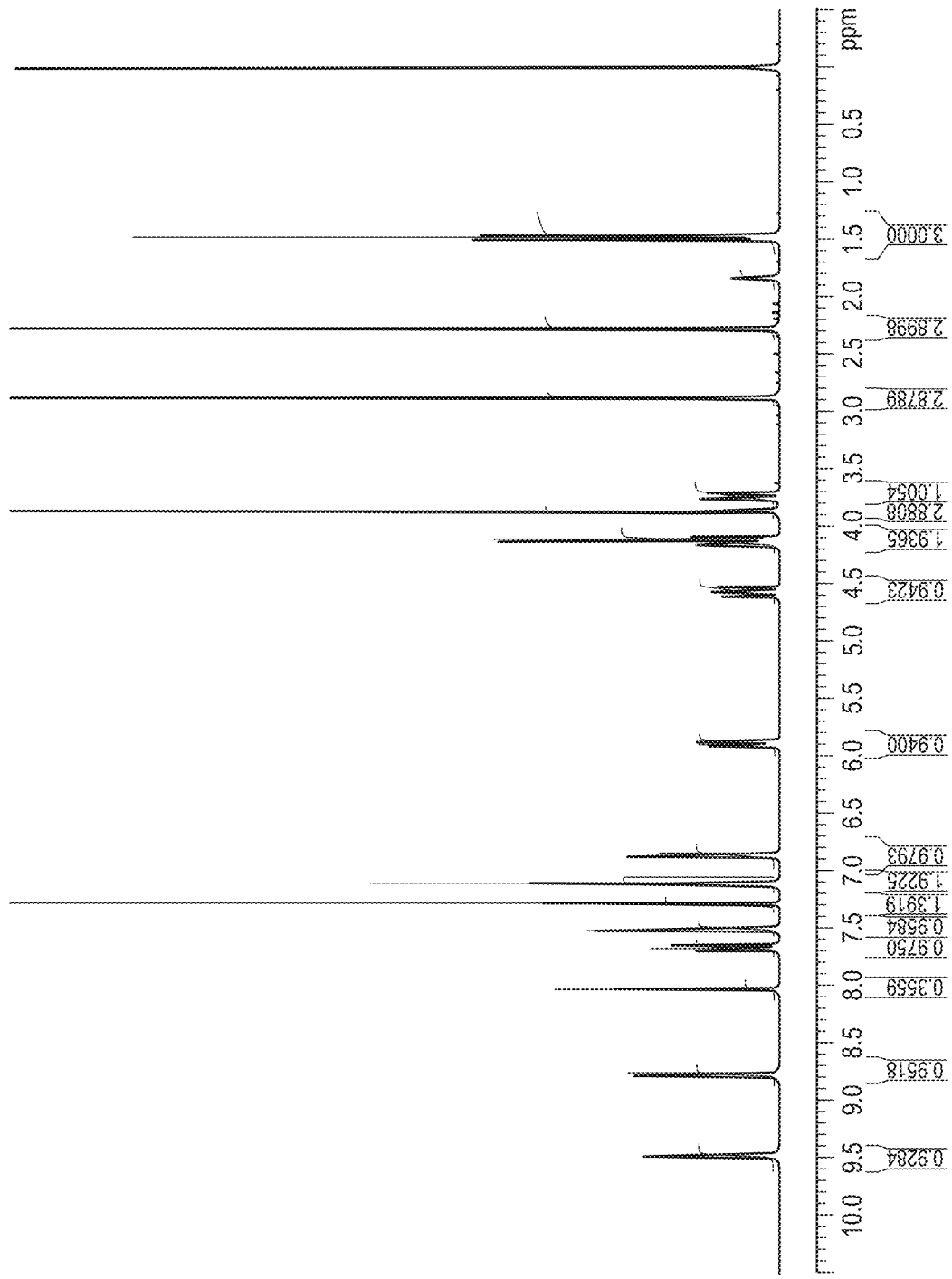
FIG. 14 $^1$H-NMR plot of apremilast Form J.

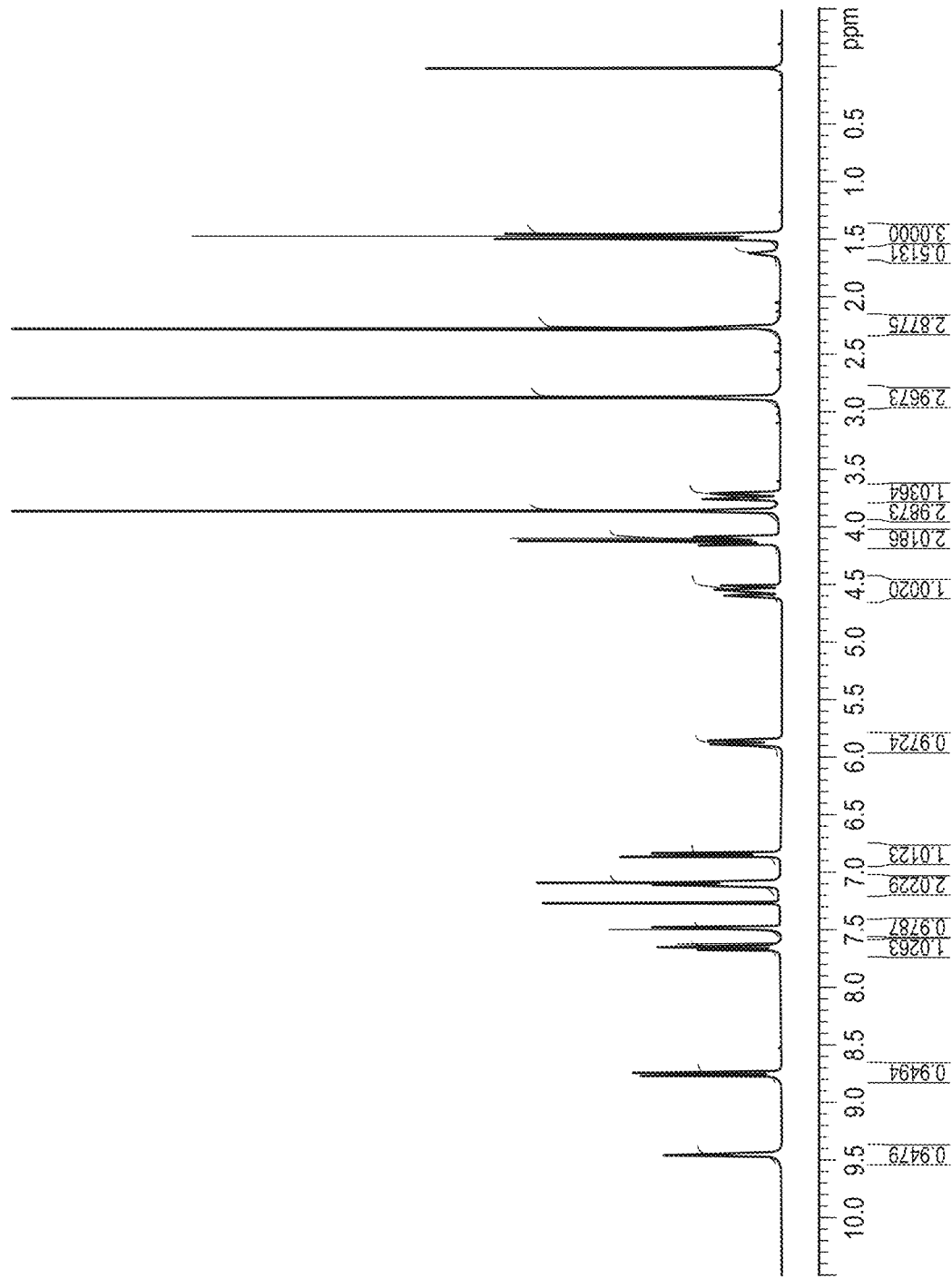

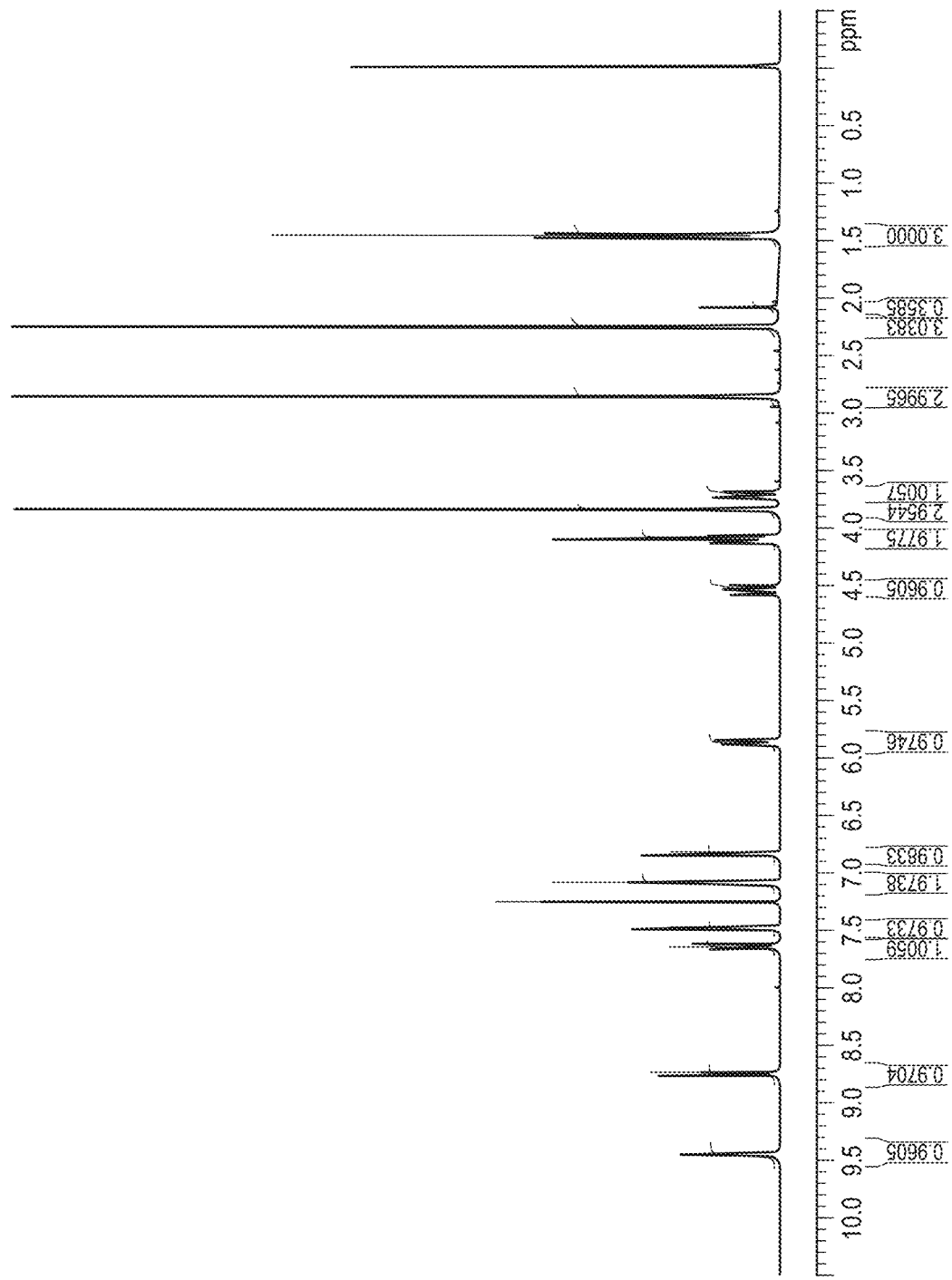
FIG. 16 1H-NMR plot of apremilast Form M.

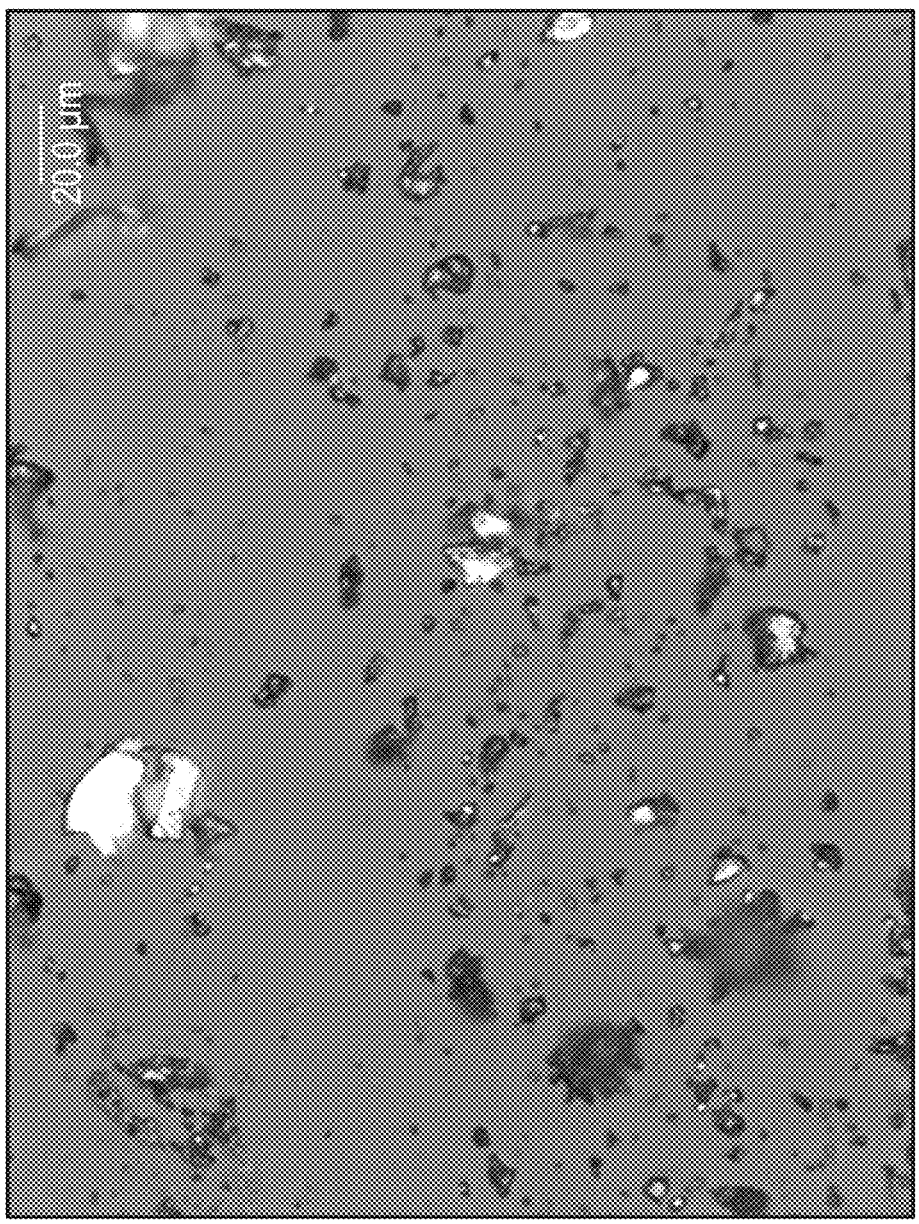
FIG. 17 Optical Microscopic Image of apremilast Form H.

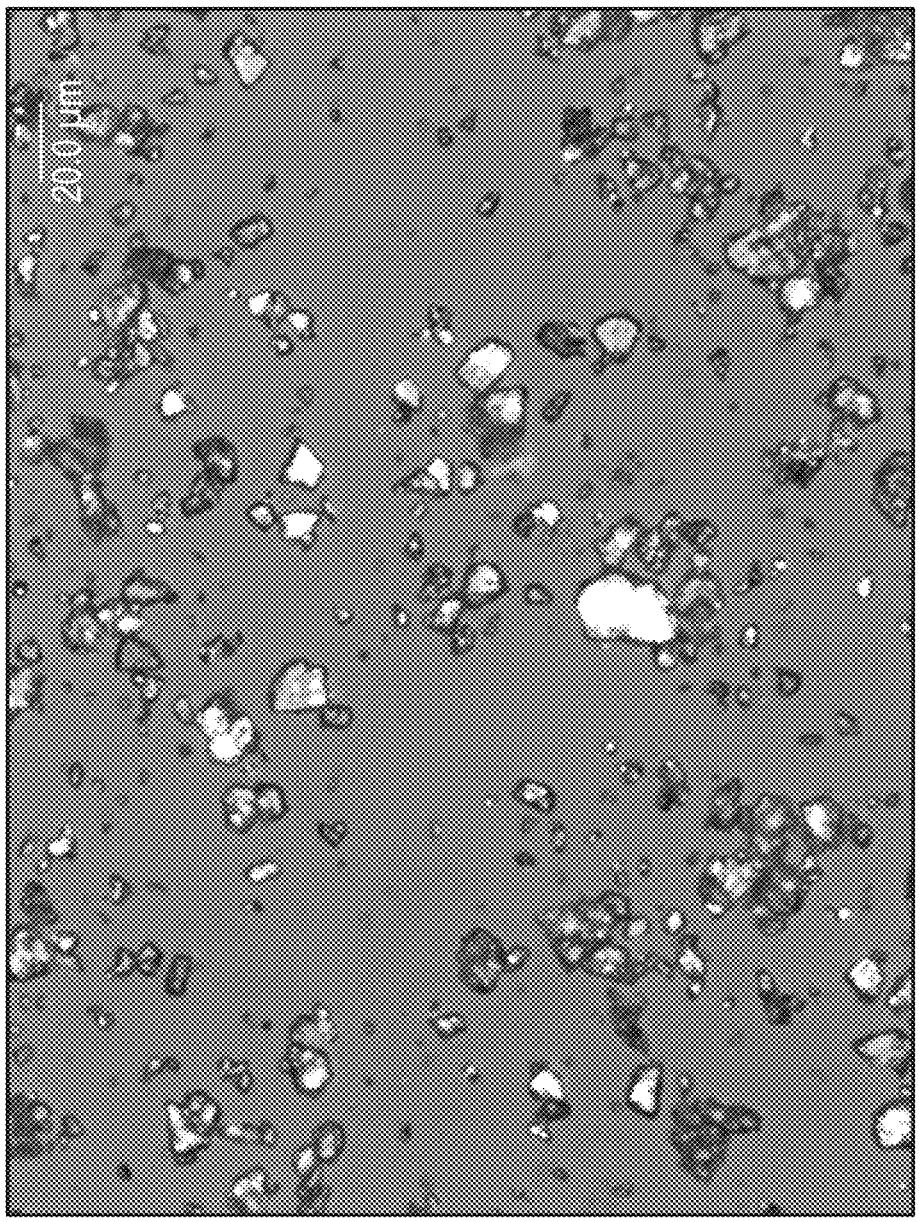
FIG. 18 Optical Microscopic Image of apremilast Form J.

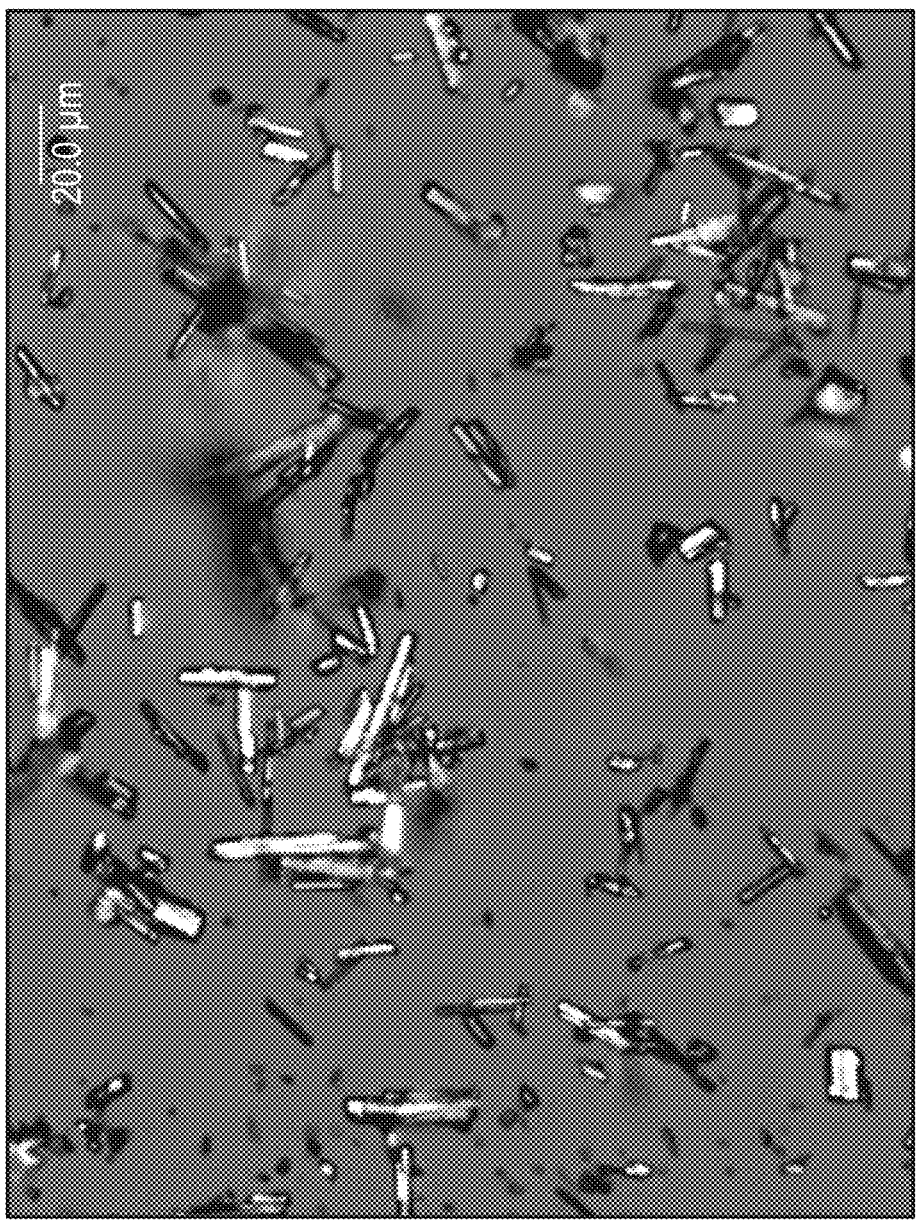
FIG. 19 Optical Microscopic Image of apremilast.

FORMS OF APREMILAST

CROSS-REFERENCE TO RELATED APPLICATIONS

This application is a divisional of U.S. patent application Ser. No. 16/212,264 filed on Dec. 6, 2018, which is a divisional of U.S. patent application Ser. No. 15/186,687, filed on Jun. 20, 2016, issued as U.S. Pat. No. 10,196,355.

FIELD OF THE DISCLOSURE

The present disclosure relates to novel forms of apremilast, and methods for making the same. The present disclosure also relates to pharmaceutical compositions comprising the novel forms of apremilast and methods for treating disease using such compositions.

BACKGROUND OF THE DISCLOSURE

Apremilast refers to (+)-2-[1-(3-ethoxy-4-methoxyphenyl)-2-methylsulfonylethyl]-4-acetylaminoisoindoline-1,3-dione and has the following structure:

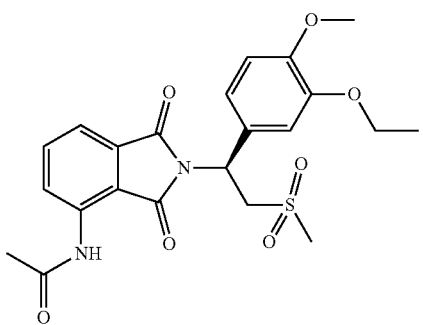 [SMILES: CCOc1cc([C@@H](CS(C)(=O)=O)N2C(=O)c3cccc(NC(C)=O)c3C2=O)ccc1OC]

Apremilast is a small molecule inhibitor of phosphodiesterase (PDE4). Apremilast inhibits PDE4 and inhibits spontaneous production of TNF-alpha from human rheumatoid synovial cells. Apremilast also has anti-inflammatory activity. In 2014, Apremilast was approved by the United States Food and Drug administration for the treatment of active psoriatic arthritis and moderate to severe plaque psoriasis. It is available under the trade name of OTEZLA® as an inhibitor of phosphodieasterase 4 (PDE4) and OTEZLA® tablets are supplied in 10, 20, and 30 mg strengths for oral administration. Apremilast is also being evaluated for its efficacy in treating other chronic inflammatory diseases such as ankylosing spondylitis, Behcet's disease and rheumatoid arthritis.

U.S. Pat. No. 6,020,358 describes racemic 2-[1-(3-ethoxy-4-methoxy phenyl)-2-(methyl sulfonyl)ethyl]-2,3-dihydro-1,3-dioxo-1H-isoindol-4-yl]acetamide and process for its preparation. U.S. Pat. No. 7,427,638 describes stereomerically pure (+)-2-[1-(3-ethoxy-4-methoxyphenyl)-2-methylsulfonylethyl]-4-acetylaminoisoindoline-1,3-dione, substantially free of its (−) isomer, or a pharmaceutically acceptable metabolite, salt, solvate or hydrate, thereof and its pharmaceutical composition. WO 2012/097116 and U.S. 2014/0081032 describe processes for the preparation of isoindoline compounds and their isotopologues, including apremilast. U.S. 2013/0217918 describes processes for enantioselective preparation of arylmethanesulfonylethylamines using chiral auxiliaries (S)-1-(3-ethoxy-4-methoxyphenyl)-2-methanesulfonylethylamine, which is used for the preparation of apremilast. WO 2009/120167 and U.S. Pat. No. 7,893,101 describe various solid forms comprising apremilast including Forms A, B, C, D, E, F and G. WO 2014/072259 describes an anhydrous form of apremilast. U.S. 2015/0283249 describes an amorphous form of apremilast. All references cited herein, including the apremilast products associated with the above-mentioned trade names, are incorporated herein by reference in their entireties.

The preparation and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. The importance of studying polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed. The preparation of solid forms is of great importance in the development of a safe, effective, stable and marketable pharmaceutical compound. Therefore, provided herein are six novel forms of apremilast, pharmaceutical compositions comprising the novel forms of apremilast and methods for treating disease using such compositions.

SUMMARY OF THE DISCLOSURE

The present disclosure is directed to six novel forms of apremilast: five crystalline forms and an amorphous form. The crystalline forms are identified herein as Forms H, I, J, K and M. The present disclosure is further directed to processes for the preparation of the novel forms of apremilast as herein described.

Illustrative of the present disclosure is a pharmaceutical composition comprising at least one pharmaceutically acceptable excipient and any of the forms of apremilast as herein described. Illustrative of the present disclosure is a process for making a pharmaceutical composition comprising mixing any of the forms of apremilast as herein described and at least one pharmaceutically acceptable excipient.

Exemplifying the present disclosure are methods of treating disease, comprising administering to a subject in need thereof, one or more of the forms of apremilast or pharmaceutical compositions described above.

BRIEF DESCRIPTION OF THE DRAWINGS

FIG. 1 provides a representative XRPD pattern of apremilast Form H, expressed in terms of ° 2θ.

FIG. 2 provides a representative XRPD pattern of apremilast Form I, expressed in terms of ° 2θ.

FIG. 3 provides a representative XRPD pattern of apremilast Form J, expressed in terms of ° 2θ.

FIG. 4 provides a representative XRPD pattern of apremilast Form K, expressed in terms of ° 2θ.

FIG. 5 provides a representative XRPD pattern of apremilast Form M, expressed in terms of ° 2θ.

FIG. 6 provides a representative X-ray Powder Diffraction ("XRPD") pattern of apremilast, expressed in terms of ° 2θ.

FIG. 7 provides a representative Differential Scanning calorimetry ("DSC") and Thermal Gravimetric Analysis ("TGA") plot of apremilast Form H.

FIG. 8 provides a representative Differential Scanning calorimetry ("DSC") and Thermal Gravimetric Analysis ("TGA") plot of apremilast Form I.

FIG. 9 provides a representative Differential Scanning calorimetry ("DSC") and Thermal Gravimetric Analysis ("TGA") plot of apremilast Form J.

FIG. 10 provides a representative Differential Scanning calorimetry ("DSC") and Thermal Gravimetric Analysis ("TGA") plot of apremilast Form K.

FIG. 11 provides a representative Differential Scanning calorimetry ("DSC") and Thermal Gravimetric Analysis ("TGA") plot of apremilast Form M.

FIG. 12 provides a representative Proton Nuclear Magnetic Resonance ($^1$H-NMR) plot of apremilast Form H.

FIG. 13 provides a representative Proton Nuclear Magnetic Resonance ($^1$H-NMR) plot of apremilast Form I.

FIG. 14 provides a representative Proton Nuclear Magnetic Resonance ($^1$H-NMR) plot of apremilast Form J.

FIG. 15 provides a representative Proton Nuclear Magnetic Resonance ($^1$H-NMR) plot of apremilast Form K.

FIG. 16 provides a representative Proton Nuclear Magnetic Resonance ($^1$H-NMR) plot of apremilast Form M.

FIG. 17 provides a representative Optical Microscopic Image of apremilast Form H.

FIG. 18 provides a representative Optical Microscopic Image of apremilast Form J.

FIG. 19 provides a representative Optical Microscopic Image of apremilast.

DETAILED DESCRIPTION OF THE DISCLOSURE

The present disclosure is directed to novel forms of apremilast, as herein described in detail. More particularly, the present disclosure is directed to novel Forms H, I, J, K and M of apremilast and an amorphous form of apremilast.

The present disclosure is further directed to processes for the preparation of the novel forms of apremilast, as described in more detail in the Examples which follow herein.

The present disclosure is further directed to pharmaceutical compositions comprising one or more of the novel forms of apremilast. The present disclosure is further directed to a method of treating pain comprising administering to a subject in need thereof, one or more of the novel forms of apremilast.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context and unless otherwise specified, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance be about 99%, 98%, 97%, 96%, 95%, 94%, 93%, 92%, 91% or 90% physically and/or chemically pure.

As used herein and unless otherwise specified, the term "composition" is intended to encompass a product comprising the specified ingredients in the specified amounts, as well as any product which results, directly or indirectly, from combinations of the specified ingredients in the specified amounts.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., Remington: The Science and Practice of Pharmacy, 21st edition, Lippincott, Williams and Wilkins, Baltimore, Md. (2005); The United States Pharmacopeia, 23rd ed., 1843-1844 (1995).

As used herein and unless otherwise specified, the term "crystal forms," "crystalline forms" and related terms herein refer to solid forms that are crystalline. Crystal forms include single-component crystal forms and multiple-component crystal forms, and include, but are not limited to, polymorphs, solvates, hydrates, and/or other molecular complexes. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein, the term "excipient" refers to a pharmaceutically acceptable organic or inorganic carrier substance. Excipients may be natural or synthetic substances formulated alongside the active ingredient of a medication, included for the purpose of bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance, such as by facilitating powder flowability or non-stick properties, in addition to aiding in vitro stability such as prevention of denaturation over the expected shelf life.

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, the term "pharmaceutically acceptable salts" refer to salts prepared from pharmaceutically acceptable non-toxic acids or bases including inorganic acids and bases and organic acids and bases.

As used herein and unless otherwise specified, the terms "polymorphs," "polymorphic forms" and related terms herein, refer to two or more crystal forms that consist essentially of the same molecule, molecules, and/or ions. Like different crystal forms, different polymorphs may have different physical properties such as, e.g., melting temperature, heat of fusion, solubility, dissolution properties and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (e.g., one polymorph might be more likely to form solvates or might be difficult to filter and wash free of impurities, and particle shape and size distribution might be different between polymorphs).

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "solid form" and related terms refer to a physical form which is not predominantly in a liquid or a gaseous state. Solid forms may be crystalline, amorphous or mixtures thereof. In particular embodiments, solid forms may be liquid crystals.

As used herein and unless otherwise specified, the terms "solvate" and "solvated," refer to a crystal form of a substance which contains solvent. The terms "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

The term "subject" as used herein refers to an animal, preferably a mammal, most preferably a human, who has been the object of treatment, observation or experiment. Preferably, the subject has experienced and/or exhibited at least one symptom of the disease or disorder to be treated and/or prevented. Further, a subject may not have exhibited any symptoms of the disorder, disease or condition to be treated and/prevented, but has been deemed by a physician, clinician or other medical professional to be at risk for developing said disorder, disease or condition.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

Techniques for characterizing crystal and amorphous forms include, but are not limited to differential scanning calorimetry (DSC), thermal gravimetric analysis (TGA), X-ray powder diffractometry (XRPD), proton nuclear magnetic resonance ($^1$H-NMR) and Optical Microscopy.

DSC data were collected using a TA Instruments Q10 DSC. Approximately, samples (2-8 mg) were placed in unsealed but covered hermetic alodined aluminum sample pans and scanned from 30 to 300° C. at a rate of 10° C./min under a nitrogen purge of 50 mL/min.

TGA data were collected using a TA Instruments TGA Q500. Approximately, samples (5-10 mg) were placed in an open, pre-tared aluminum sample pan and scanned from 25 to 300° C. at a rate of 10° C./min using a nitrogen purge at 60 mL/min.

XRPD patterns were obtained using a Bruker D8 Advance equipped with a Cu Kα radiation source (λ=1.54° A), a 9-position sample holder and a LYNXEYE super speed detector. Samples were placed on zero-background, silicon plate holders for analysis. One skilled in the art would recognize that the ° 2θ values and the relative intensity values are generated by performing a peak search on the measured data and the d-spacing values are calculated by the instrument from the ° 2θ values using Bragg's equation. One skilled in the art would further recognize that the relative intensity for the measured peaks may vary as a result of sample preparation, orientation and instrument used, for example.

$^1$H-NMR data were collected using a Bruker Avance 300 MHz NMR equipped with TopSpin software. Samples were prepared by dissolving the compound in deuterated dimethylsulfoxide with 0.05% (v/v) tetramethylsilane (TMS). Spectra were collected at ambient temperature. The number of scans was 16 for $^1$H-NMR.

Optical microscopy data were collected using an Olympus BX53 polarized light microscope equipped with a PAXcam 3 digital microscope camera.

The novel forms of apremilast of the present disclosure may be prepared directly or indirectly from apremilast. Examples 1-6, which follow herein, provide embodiments of the preparation of the novel forms of apremilast.

Apremilast Form H, a solvate, is a unique crystalline phase. A DSC thermogram and TGA plot, FIG. 7, shows a thermal event at 113° C. and a weight loss of about 2% when heated from 30 to 125° C. Apremilast Form H is further characterized by its XRPD pattern peaks and/or d-spacing values, as listed in Table 1 below. FIG. 1 is a representative XPRD pattern for a representative sample of apremilast Form H made according to Example 1. Apremilast Form H is stable under stressed conditions, i.e. at under 45° C. and humid conditions (relative humidity>95%).

TABLE 1

Peak list for Form H diffractogram

| Angle (2θ) degree | Intensity % | d value (Å) |
|---|---|---|
| 7.47 | 100 | 11.820 |
| 11.26 | 30.2 | 7.852 |
| 14.02 | 21.7 | 6.311 |
| 15.33 | 25.6 | 5.776 |
| 16.42 | 28.0 | 5.394 |
| 17.74 | 53.6 | 4.996 |
| 19.41 | 36.1 | 4.570 |
| 20.81 | 15.6 | 4.266 |
| 21.42 | 31.0 | 4.146 |
| 22.53 | 34.1 | 3.944 |
| 23.50 | 31.1 | 3.783 |
| 24.80 | 22.9 | 3.587 |
| 25.50 | 26.1 | 3.490 |
| 26.38 | 73.9 | 3.376 |
| 27.55 | 18.8 | 3.235 |
| 29.01 | 14.7 | 3.076 |

Apremilast Form I, a solvate, is a unique crystalline phase. A DSC thermogram and TGA plot, FIG. 8, shows a thermal event at 129° C. and a weight loss of about 2.8% when heated from 30 to 140° C. Apremilast Form I is further characterized by its XRPD pattern peaks and/or d-spacing values, as listed in Table 2 below. FIG. 2 is a representative XRPD pattern for a representative sample of apremilast Form I made according to Example 2. Apremilast Form I is stable under stressed conditions, i.e. at under 45° C. and humid conditions (relative humidity>95%).

TABLE 2

Peak list for Form I diffractogram

| Angle (2θ) degree | Intensity % | d value (Å) |
|---|---|---|
| 7.64 | 37.9 | 11.558 |
| 11.47 | 27.8 | 7.712 |
| 14.18 | 17.6 | 6.243 |
| 15.47 | 23.5 | 5.725 |
| 16.59 | 32.8 | 5.341 |
| 17.93 | 51.6 | 4.944 |
| 19.53 | 25.6 | 4.541 |
| 20.44 | 20.2 | 4.341 |
| 21.59 | 31.5 | 4.113 |
| 22.65 | 39.3 | 3.922 |
| 23.64 | 32.8 | 3.760 |
| 24.96 | 35.2 | 3.564 |
| 25.62 | 31.8 | 3.474 |
| 26.51 | 100 | 3.360 |
| 27.70 | 28.5 | 3.217 |
| 29.16 | 25.5 | 3.060 |

Apremilast Form J, a solvate, is a unique crystalline phase. A DSC thermogram and TGA plot, FIG. 9, shows a thermal event at 151° C. and a weight loss of about 3.8% when heated from 31 to 140° C. Apremilast Form J is further characterized by its XRPD pattern peaks and/or d-spacing values, as listed in Table 3 below. FIG. 3 is a representative XRPD pattern for a representative sample of apremilast Form J made according to Example 3. Apremilast Form J loses formic acid when dried under vacuum at 45° C. and undergoes a form change, resulting in the anhydrous Form K described herein.

TABLE 3

Peak list for Form J diffractogram

| Angle (2θ) degree | Intensity % | d value (Å) |
|---|---|---|
| 10.81 | 100 | 8.180 |
| 12.72 | 33.6 | 6.954 |
| 13.12 | 56.3 | 6.740 |
| 13.35 | 18.9 | 6.626 |
| 14.47 | 29.6 | 6.116 |
| 18.28 | 12.4 | 4.850 |
| 19.35 | 19.7 | 4.584 |
| 20.76 | 22.1 | 4.275 |
| 21.21 | 79.1 | 4.185 |
| 21.55 | 24.0 | 4.120 |
| 22.08 | 25.5 | 4.022 |
| 22.33 | 31.0 | 3.978 |
| 24.74 | 27.4 | 3.596 |
| 26.40 | 17.4 | 3.373 |
| 26.66 | 32.1 | 3.341 |
| 27.26 | 91.0 | 3.268 |

Apremilast Form K, an anhydrous form, is a unique crystalline phase. A DSC thermogram and TGA plot, FIG. 10, shows the presence of water in the sample, which confirms that Form K picks up moisture when exposed to air. Apremilast Form K is further characterized by its XRPD pattern peaks and/or d-spacing values, as listed in Table 4 below. FIG. 4 is a representative XRPD pattern for a representative sample of apremilast Form K made according to Example 4. Form K does not undergo a significant change when exposed to high humidity, however the XRPD pattern peaks are found to be sharp.

TABLE 4

Peak list for Form K diffractogram

| Angle (2θ) degree | Intensity % | d value (Å) |
|---|---|---|
| 11.40 | 100 | 7.756 |
| 13.32 | 19.5 | 6.640 |
| 13.66 | 42.7 | 6.477 |
| 14.02 | 9.4 | 6.313 |
| 14.83 | 40.6 | 5.968 |
| 16.29 | 10.6 | 5.437 |
| 17.72 | 4.7 | 5.002 |
| 18.01 | 14.2 | 4.923 |
| 18.83 | 15.8 | 4.708 |
| 22.37 | 22.3 | 3.972 |
| 22.86 | 20.1 | 3.887 |
| 23.24 | 14.5 | 3.825 |
| 25.30 | 11.7 | 3.517 |
| 25.74 | 9.0 | 3.459 |
| 26.67 | 13.5 | 3.340 |
| 27.13 | 37.0 | 3.285 |

Apremilast Form M, a solvate, is a unique crystalline phase. Apremilast Form M is further characterized by its XRPD pattern peaks and/or d-spacing values, as listed in Table 5 below. FIG. 5 is a representative XRPD pattern for a representative sample of apremilast Form M made according to Example 5. Form M tends to lose some of the acetic acid when dried under vacuum at 45° C. and results in a semi-crystalline form. The semi-crystalline form reverts back to Form M when exposed to humidity. Form M upon prolonged slurry converts to apremilast as shown in FIG. 6.

TABLE 5

Peak list for Form M diffractogram

| Angle (2θ) degree | Intensity % | d value (Å) |
|---|---|---|
| 7.35 | 100 | 12.022 |
| 9.43 | 27.6 | 9.375 |
| 11.34 | 63.6 | 7.796 |
| 13.67 | 25.5 | 6.473 |
| 14.89 | 21.8 | 5.944 |
| 16.14 | 45.6 | 5.486 |
| 17.52 | 48 | 5.059 |
| 18.00 | 19.8 | 4.925 |
| 18.85 | 21.4 | 4.705 |
| 20.95 | 27.1 | 4.238 |
| 21.97 | 29.2 | 4.042 |
| 22.53 | 17.1 | 3.943 |
| 23.04 | 24.9 | 3.857 |
| 24.86 | 28.2 | 3.579 |
| 25.81 | 57.6 | 3.449 |
| 27.09 | 23.1 | 3.289 |

The present disclosure also encompasses pharmaceutical compositions comprising apremilast as disclosed herein. As used herein, the term "pharmaceutical compositions" includes pharmaceutical formulations like tablets, pills, powders, liquids, suspensions, emulsions, granules, capsules, suppositories, or injection preparations.

Pharmaceutical compositions containing the apremilast of the present disclosure may be prepared by using diluents or excipients such as fillers, bulking agents, binders, wetting agents, disintegrating agents, surface active agents, and lubricants. Various modes of administration of the pharmaceutical compositions of the present disclosure can be selected depending on the therapeutic purpose, for example tablets, pills, powders, liquids, suspensions, emulsions, granules, capsules, suppositories, or injection preparations.

In another general aspect, there is provided a pharmaceutical composition comprising an amorphous form of apremilast and one or more pharmaceutically acceptable carriers, excipients and diluents.

In another general aspect, there is provided a pharmaceutical composition comprising an amorphous form of apremilast and one or more pharmaceutically acceptable carriers, excipients and diluents. In general, the pharmaceutical composition comprising an amorphous form of apremilast comprises at least one polymer selected from hydroxypropyl methylcellulose acetate succinate, hydroxypropyl methyl cellulose, methacrylic acid copolymers, and polyvinyl pyrrolidone.

In another general aspect, there is provided a pharmaceutical composition comprising an amorphous form of apremilast free from residual solvents and one or more pharmaceutically acceptable carriers, excipients or diluents.

In another general aspect, there is provided a pharmaceutical composition comprising a stable amorphous form of apremilast and at least one polymer having one or more pharmaceutically acceptable carriers, excipients or diluents.

The present disclosure also describes pharmaceutical compositions comprising one or more of the apremilast novel forms as herein described in association with conventional excipients. These compositions may be in dosage forms such as, but not limited to, tablets, pills, capsules, powders, granules, sterile parenteral solutions or suspensions, metered aerosol or liquid sprays, drops, ampoules, autoinjector devices or suppositories; for oral, parenteral, intranasal, sublingual or rectal administration, or for administration by inhalation or insufflation.

To prepare a pharmaceutical composition of the present disclosure, any one or more of the apremilast novel forms as herein described is intimately admixed with a pharmaceutical excipient according to conventional pharmaceutical compounding techniques, which excipient may take a wide variety of forms depending of the form of preparation desired for administration (e.g. oral or parenteral). Suitable pharmaceutically acceptable excipients include those known in the art and those yet to be discovered. Descriptions of some of these pharmaceutically acceptable excipients may be found in *The Handbook of Pharmaceutical Excipients* and the Pharmaceutical Society of Great Britain. The pharmaceutical compositions of the present disclosure may be prepared according to any method known in the art as well as yet to be discovered improvements thereto. Methods of formulating pharmaceutical compositions have been described in numerous publications such as *Pharmaceutical Dosage Forms: Tablets, Second Edition, Revised and Expanded*, Volumes 1-3; *Pharmaceutical Dosage Forms: Parenteral Medications*, Volumes 1-2; and *Pharmaceutical Dosage Forms: Disperse Systems*, Volumes 1-2.

The oral formulations of the present disclosure may be coated or otherwise compounded to provide a dosage form affording the advantage of prolonged action. The sustained release dosage forms may optionally comprise particles containing any one or more of the apremilast forms as herein described. Preferably, the particles are film coated with a material that permits release of the active at a sustained rate in an aqueous medium. The film coat is chosen so as to achieve, in combination with the other stated properties, desired release properties. The sustained release coating formulations of the present disclosure should preferably be capable of producing a strong, continuous film that is smooth and elegant, capable of supporting pigments and other coating additives, non-toxic, inert and tack-free. The sustained release formulations of the present disclosure preferably slowly release the active agent(s), e.g., when ingested and exposed to gastric fluids, and then to intestinal fluids. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate. Sustained release dosage forms according to the present disclosure may also be prepared as osmotic dosage formulations known in the art as well as improvements thereto.

The liquid forms in which the novel compositions of the present disclosure may be incorporated for administration orally or by injectable include, aqueous solutions, suitably flavored syrups, aqueous or oil suspensions, and flavored emulsions with edible oils as well as elixirs and similar pharmaceutical vehicles. The liquid forms may include suitably flavored suspending or dispersing agents such as the synthetic and natural gums. For parenteral administration, sterile suspensions and solutions are desired. Isotonic preparations which generally contain suitable preservative are employed when intravenous administration is desired.

The formulations of the present disclosure may be formulated as a pharmaceutical suppository for rectal administration comprising a suitable suppository base, and any one or more of the apremilast novel forms as herein described. This includes the preparation of sustained release suppository formulations as described in U.S. Pat. No. 5,215,758.

The compounds of the present disclosure may be administered in intranasal form via topical use of suitable intranasal vehicles, or via transdermal skin patches well known to those of ordinary skill in the art. To be administered in the form of a transdermal delivery system, the dosage administration will be continuous rather than intermittent throughout the dosage regimen.

The present disclosure provides for a method of treating pain by administering to a subject in need thereof the dosage forms described above which contain any one or more of the apremilast novel forms as herein described. The dosage of the products may be varied over a wide range. Optimal dosages and dosage regimens to be administered may be readily determined by those skilled in the art, and will vary with the mode of administration, the strength of the preparation and the advancement of the disease condition. In addition, factors associated with the particular subject being treated, including subject's sex, age, weight, diet, physical activity, time of administration and concomitant diseases, will result in the need to adjust dosages and/or regimens.

EXAMPLES

The disclosure is illustrated by the following examples.

The following examples are set forth to aid in the understanding of the disclosure, and are not intended and should not be construed to limit in any way the disclosure set forth in the claims which follow thereafter. Although illustrated and herein described with reference to certain specific embodiments, the present disclosure is nevertheless not intended to be limited to the details shown. Rather, various modifications may be made in the details within the scope and range of equivalents of the claims and without departing from the spirit of the disclosure.

Example 1

Preparation of Apremilast Form H

About 100 mg of apremilast and about 1 mL of dimethylformamide and water in a 4:1 ratio are added to a vial. The mixture is stirred at about room temperature. The resulting solids are analyzed by XRPD and identified as apremilast Form H.

Example 2

Preparation of Apremilast Form I

About 100 mg of apremilast and about 1 mL of dimethylacetamide are added to a vial. The mixture is stirred at about room temperature. The resulting solids are analyzed by XRPD and identified as apremilast Form I.

Example 3

Preparation of Apremilast Form J

About 100 mg of apremilast and about 1 mL of formic acid and water in a 4:1 ratio are added to a vial. The mixture is stirred at about room temperature. The resulting solids are analyzed by XRPD and identified as apremilast Form J.

Example 4

Preparation of Apremilast Form K

Form J is dried at about 50° C. under vacuum. The resulting solids are analyzed by XRPD and identified as apremilast Form K.

Example 5

Preparation of Apremilast Form M

About 150 mg of apremilast is dissolved in about 0.2 mL of acetic acid. About 1 mL of ice cold heptane is added to the mixture. The mixture is stirred at about 0° C. The resulting solids are analyzed by XRPD and identified as apremilast Form M.

Example 6

Preparation of Apremilast Form H

About 150 mg of apremilast is dissolved in about 0.2 mL of dimethylformamide. About 1 mL of ice cold tert-butyl methyl ether is added to the mixture. The mixture is stirred at about 0° C. The resulting solids are analyzed by XRPD and identified as apremilast Form H.

Example 7

Preparation of Apremilast Form K

About 1 g of apremilast is dissolved in about 1 mL of formic acid at about 55° C. About 1 mL of water is added slowly to the mixture with continuous stirring. A turbid solution is formed. About 1 mL of water was again added to the reaction mixture, resulting in a sticky material. The reaction vial is placed in ice bath until the sticky material is solidified. The solid is crushed and the resultant mixture is stirred for about 3 days at about room temperature. The resulting solids are analyzed by XRPD and identified as apremilast Form K.

Example 8

Preparation of Apremilast Form J

About 1 g of apremilast is dissolved in about 1 mL of formic acid at about 55° C. About 3 mL of ice cold water is added slowly to the mixture with continuous stirring. A sticky material is formed. The reaction vial is placed in ice bath and the resultant mixture is stirred for about 3 days at about room temperature. The resulting solids are analyzed by XRPD and identified as apremilast Form J.

Example 9

Preparation of Apremilast Form M

About 1 g of apremilast is dissolved in about 5 mL of acetic acid at about 55° C. About 5 mL of ice cold heptane is added slowly to the mixture with continuous stirring. A bi-phasic solution is formed. The reaction vial is placed in ice bath. The solution is stirred for about 3 days at about room temperature. The resulting solids are analyzed by XRPD and identified as apremilast and apremilast Form M.

What is claimed is:

1. Apremilast dimethylacetamide solvate Form I.
2. The apremilast dimethylacetamide solvate Form I according to claim 1 that has an X-ray powder diffraction pattern comprising peaks, in terms of 2-theta, at about 26.51 and about 17.93.
3. The apremilast dimethylacetamide solvate Form I according to claim 2, further comprising peaks, in terms of 2-theta, at about 22.65, about 7.64, and about 24.96.
4. The apremilast dimethylacetamide solvate Form I according to claim 1 that is characterized by an endothermic event at about 129° C.
5. The apremilast dimethylacetamide solvate Form I according to claim 1 that is characterized by an endothermic event onset at about 126° C.
6. A composition comprising the apremilast dimethylacetamide solvate Form I according to claim 1.
7. The composition according to claim 6, wherein the composition is a pharmaceutical composition further comprising at least one pharmaceutically acceptable excipient.
8. A method of treating a disease selected from the group consisting of psoriatic arthritis, plaque psoriasis, and Behcet's disease comprising administering the pharmaceutical composition according to claim 7 to a subject in need thereof.
9. A method of making apremilast dimethylacetamide solvate Form I according to claim 1, comprising exposing a starting material comprising apremilast to dimethylacetamide to yield apremilast dimethylacetamide solvate Form I.

* * * * *